(12) United States Patent
Kim et al.

(10) Patent No.: US 7,785,625 B2
(45) Date of Patent: *Aug. 31, 2010

(54) LIPOPHILIC-COATED MICROPARTICLE CONTAINING A PROTEIN DRUG AND FORMULATION COMPRISING SAME

(75) Inventors: Myung-Jin Kim, Taejon (KR); Sun-Jin Kim, Seoul (KR); Kyu-Chan Kwon, Taejon (KR); Joon Kim, Taejon (KR)

(73) Assignee: LG Life Sciences, Limited, Seoul (KR)

( * ) Notice: Subject to any disclaimer, the term of this patent is extended or adjusted under 35 U.S.C. 154(b) by 766 days.

This patent is subject to a terminal disclaimer.

(21) Appl. No.: 11/024,362

(22) Filed: Dec. 28, 2004

(65) Prior Publication Data

US 2005/0158392 A1    Jul. 21, 2005

Related U.S. Application Data

(63) Continuation-in-part of application No. 10/160,784, filed on Jun. 3, 2002, now abandoned, which is a continuation-in-part of application No. 09/648,196, filed on Aug. 25, 2000, now abandoned, which is a continuation of application No. PCT/KR00/00025, filed on Jan. 14, 2000, now abandoned.

(51) Int. Cl.
*A61K 9/19* (2006.01)
*A61K 9/22* (2006.01)

(52) U.S. Cl. .................. 424/468; 424/489; 424/499; 424/502; 514/2; 514/12

(58) Field of Classification Search .................. None
See application file for complete search history.

(56) References Cited

U.S. PATENT DOCUMENTS

| | | | |
|---|---|---|---|
| 5,091,187 A | 2/1992 | Haynes | |
| 5,416,071 A | 5/1995 | Igari et al. | |
| 5,536,508 A | 7/1996 | Canal et al. | |
| 5,707,644 A * | 1/1998 | Illum | 424/434 |
| 5,759,566 A | 6/1998 | Poli et al. | |
| 5,858,398 A | 1/1999 | Cho | |
| 7,276,251 B2 * | 10/2007 | Kim et al. | 424/468 |
| 2002/0058624 A1 | 5/2002 | Hanyu et al. | |

FOREIGN PATENT DOCUMENTS

| | | |
|---|---|---|
| DE | 41 23 663 | 1/1993 |
| JP | 5-97694 | 4/1993 |
| JP | 1992-283510 | 10/1993 |
| RU | 2 079 304 | 5/1997 |
| RU | 2 104 715 | 2/1998 |
| WO | 91/14454 | 10/1991 |
| WO | 92/14449 | 9/1992 |
| WO | 95/12385 | 5/1995 |
| WO | 98/09650 | 3/1998 |
| WO | 98/29099 | 7/1998 |
| WO | 98/43664 | 10/1998 |

OTHER PUBLICATIONS

M. Takenaga, et al. "Application of Lipid Microspheres to Prepare A Thromboxane A2 Receptor Antagonist Inhaler" Journal of Controlled Release, 1994, vol. 28(1-3), pp. 344-345.
Shing C. Chen, et al. "Protective Immunity Induced by Oral Immunization with a Rotavirus DNA Vaccine Encapsulated in Microparticles" Journal of Virology, Jul. 1998, pp. 5757-5761.

* cited by examiner

*Primary Examiner*—Dong Jiang
*Assistant Examiner*—Sandra Wegert
(74) *Attorney, Agent, or Firm*—Katten Muchin Rosenman LLP (57) ABSTRACT

A solid lipophilic microparticle having an average particle size ranging from 0.1 to 200 μm, comprising a lipophilic substance, hyaluronic acid or an inorganic salt thereof and an active ingredient selected from the group consisting of a protein or peptide drug, retains the full activity of the active ingredient, and when formulated in the form of an oil dispersion or oil-in-water emulsion, it releases in an in vivo environment the active ingredient in a controlled manner over a long period.

17 Claims, 3 Drawing Sheets

LIPOPHILIC-COATED MICROPARTICLE CONTAINING A PROTEIN DRUG AND FORMULATION COMPRISING SAME

CROSS-REFERENCE TO RELATED APPLICATION

The present application is a continuation-in-part of U.S. patent application Ser. No. 10/160,784, filed on Jun. 3, 2002, now abandoned, which is a continuation-in-part of U.S. patent application Ser. No. 09/648,196, filed on Aug. 25, 2000, now abandoned, which is a continuation of International Application PCT/KR 00/00025, with an international filing date of Jan. 14, 2000, now abandoned.

FIELD OF THE INVENTION

The present invention relates to a solid lipophilic microparticle comprising a lipophilic substance, hyaluronic acid or an inorganic salt thereof and an active ingredient selected from the group consisting of a protein drug and a peptide drug, wherein the active ingredient is combined with hyaluronic acid or an inorganic salt thereof and a lipophilic substance in a one or two step process and spray dried to form a solid microparticle.

BACKGROUND OF THE INVENTION

It is well known that protein drugs suffer from the problem of denaturation caused by heat, organic solvents and/or unfavorable pH (Weiqi Lu et al., *PDA J. Pharm. Sci. Tech.*, 49, 13-19 (1995)). They are usually administered by injection; however, because their in vivo activities last only for a short period of time after administration, they have to be administered repeatedly when a long-term treatment is required. For example, to treat a pituitary deficient child's dwarfism, human growth hormone (hGH) must be injected daily or every other day for a period of 6 months or more. Therefore, there have been many efforts to develop effective sustained-release formulations of protein drugs.

For example, extensive studies have been made to develop a sustained-release microparticle formulation prepared by coating a protein drug with a synthetic biodegradable polymer, e.g., polylactide, polyglycolide, poly (lactide-co-glycolide), poly-ortho-ester or polyanhydride, which continuously releases the drug or the antigen as the polymer degrades in the body (M. Chasm and R. Langer, ed., *Biodegradable Polymers as Drug Delivery Systems*, Marcel Dekker (1990); and Heller, J., *Adv. Drug Del. Rev.*, 10, 163 (1993)). Although this type of formulation has several advantages, it suffers from the serious problem that the drug undergoes denaturation upon to its contact with an organic solvent during the preparation process thereof (Park, T. G. et al., *J. Control. Rel.*, 33, 211-223 (1995)). The use of an organic solvent is unavoidable because a biodegradable polymer dissolves only in an organic solvent, e.g., methylene chloride, ethyl acetate, acetonitrile, chloroform or acetone.

In order to avoid such undesirable contact of a drug with an organic solvent, Lee et al. have prepared a microparticle by coating an protein with a water-soluble polymer to obtain a primary particle; dispersing the primary particle in an organic solvent containing a biodegradable polymer; and drying the resulting dispersion to obtain a final microparticle (Lee H. K. et al., *J. Control. Rel.*, 44, 283-294 (1997); and U.S. Pat. No. 5,753,234). However, the process of preparing such microparticle is complicated and uneconomical.

There have also been attempts to develop a sustained release formulation containing a natural polymer, e.g., gelatin, collagen, chitosan, carboxymethyl cellulose, alginate or hyaluronic acid. The natural polymer easily absorbs water to form a gel having a high viscosity which releases a drug or antigen slowly. For example, U.S. Pat. No. 5,416,017 discloses a sustained-release injection formulation of erythropoietin containing a 0.01 to 3% hyaluronic acid gel; Japanese Patent Laid-open No. 1-287041 (1989), a sustained-release injection formulation of insulin containing a 1% hyaluronic acid gel; Japanese Patent Laid-open No. 2-213 (1990), a sustained-release formulation of calcitonin, or human growth hormone containing a 5% hyaluronic acid gel; and Meyer, J. et al. (*J. Controlled Rel.*, 35, 67 (1995)), a sustained release formulation of granulocyte-colony stimulating factor (G-CSF) containing a 0.5 to 4% hyaluronic acid gel.

Such hyaluronic acid gel formulations have a sustained release effect because the protein drugs slowly pass through the gel matrix having a high viscosity. However, a gel having a hyaluronic acid concentration of several % has a high viscosity, e.g., in the order of $10^5$ to $10^7$ centipoise, which makes the injection thereof difficult. Further, since both the drug and hyaluronic acid dissolve in water, a hyaluronic acid formulation is easily diluted by the body fluid after injections with a consequential rapid release of the drug, usually within a day. For example, Japanese Patent Laid-open No. 1-287041 (1989) discloses that when a 1% hyaluronic acid gel formulation containing insulin was injected to a rabbit, the effect of lowering the blood glucose level was sustained for only 24 hours; and Meyer, J. et al. (vide supra) and U.S. Pat. No. 5,416,017, that when a 2% hyaluronic acid gel formulation containing G-CSF and a 1.5% hyaluronic acid gel formulation containing interferon-a, together with serum protein are administered to an animal, blood levels of these protein drugs suddenly drop to below 1/10 of the initial levels in 24 hours.

Benzyl hyaluronate (HYAFF™, Fidia S.P.A.), a synthetic ester prepared by esterifying natural hyaluronic acid with benzyl alcohol, does not dissolve in water but in an organic solvent such as dimethyl sulfoxide (DMSO). A solid benzyl hyaluronate microparticle formulation containing a protein drug has been prepared by the emulsion-solvent extraction method (Nightlinger, N. S. et al., *Proceed. Intern. Symp. Control Rel. Bioact. Mater.*, 22nd, Paper No., 3205 (1995); and Ilum, L. et al., *J. Controlled Rel.*, 29, 133 (1994)), which is conducted by dissolving benzyl hyaluronate in DMSO; dispersing the protein drug in the resulting solution; adding the resulting dispersion to mineral oil to form an emulsion; and adding a solvent which is miscible with DMSO, e.g., ethyl acetate, to the emulsion to extract DMSO therefrom to obtain solid microparticles comprising the protein drug and benzyl hyaluronate.

However, the benzyl hyaluronate formulation has the drawback that the protein drug can be easily denatured by the organic solvent used in the preparative step and also by hydrophobic benzyl hyaluronate itself. An in vitro release test of a benzyl hyaluronate microparticle comprising granulocyte macrophage-colony stimulating factor (GM-CSF) showed that only 25% of GM-CSF was released in the initial 2 days, and no more of GM-CSF, thereafter (Nightlinger, N. S. et al., vide supra), suggesting that most of the protein drug was denatured.

Accordingly, it is an object of the present invention to provide a microparticle having an improved stability and effective delivery of a drug.

In particular, it is an object of the present invention to provide a sustained-release drug formulation where the active ingredient is a peptide or protein drug.

It is another object to provide a procedure for formulating a peptide or protein drug into an injectable product while avoiding significant denaturation of the drug.

It is yet another object of this invention to provide method of producing an injectable formulation of a peptide or protein drug by spray drying a mixture containing the drug.

SUMMARY OF THE INVENTION

In accordance with one aspect of the present invention, there is provided a solid lipophilic microparticle comprising a lipophilic substance, hyaluronic acid or an inorganic salt thereof and an active ingredient selected from the group consisting of a protein drug and a peptide drug, wherein the active ingredient is mixed with hyaluronic acid or an inorganic salt thereof and the lipophilic substance in a one or two step process and spray dried to form a solid microparticle.

Surprisingly, the combination of the lipophilic substance and hyaluronic acid or an inorganic salt thereof acts to protect the active ingredient during formulation and prevents or minimizes denaturation of the peptide or protein content of the mixture. On the other hand, the presence of either the lipophilic substance and hyaluronic acid or an inorganic salt thereof alone does not provide this protective effect and is not useful in this procedure.

Also surprisingly, it has been found that of the many drying processes known to the art, including lyophilization, spray-freeze drying, fluid-bed granulation, fluid-bed coating and others, none provide the functionality of the present procedure in which the particles are spray dried in a one or two step process.

BRIEF DESCRIPTION OF THE DRAWINGS

The above objects and features of the present invention will become apparent from the following description of preferred embodiments taken in conjunction with the accompanying drawings, in which.

DETAILED DESCRIPTION OF THE INVENTION

Figure 1:
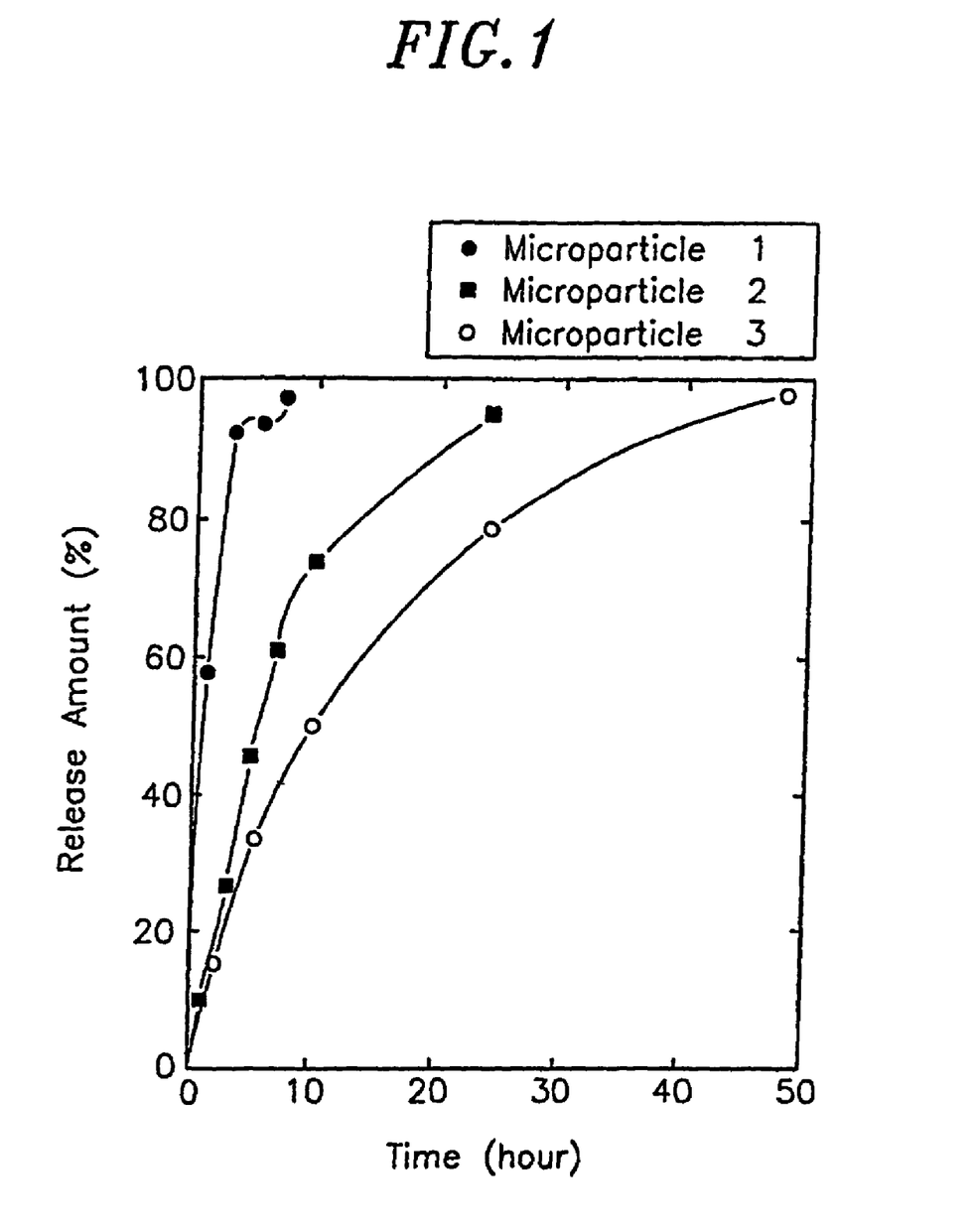
FIG. 1 shows in vitro release profiles of Microparticles 1, 2 and 3.
Figure 2A:
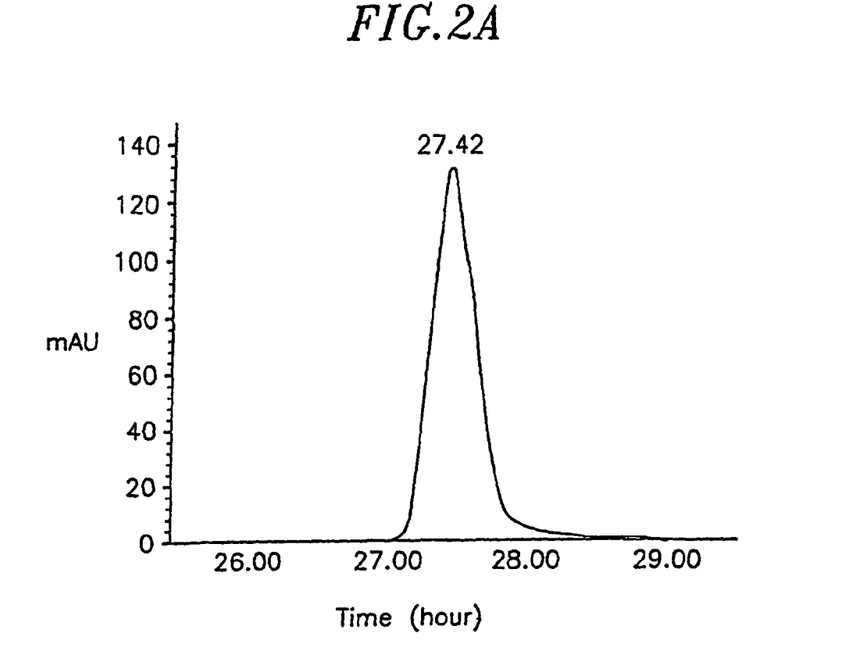
FIGS. 2A and 2B reproduce RP HPLC scans of the Microparticle 2 extract solution obtained in Test Example 2 and a standard hGH aqueous solution, respectively.
Figure 2B:
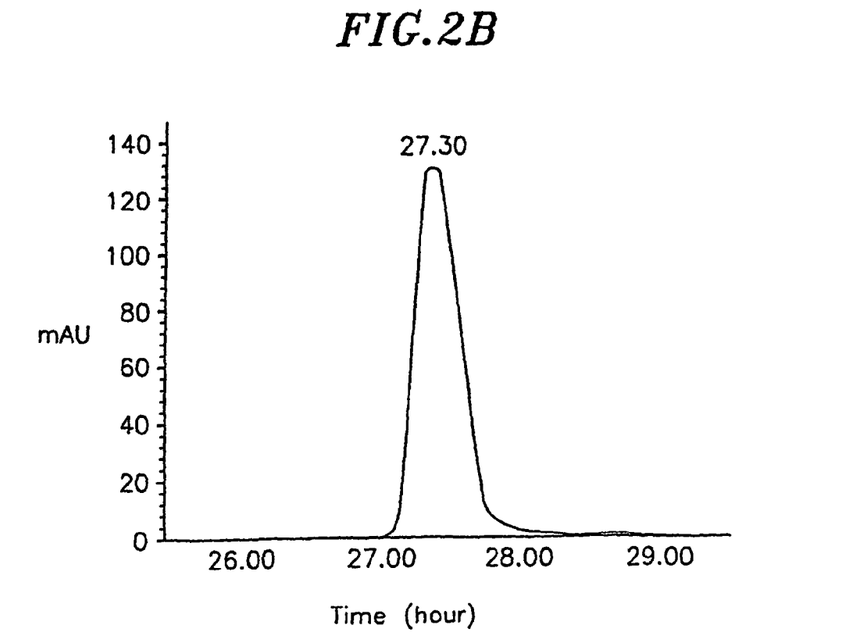
Figure 3A:
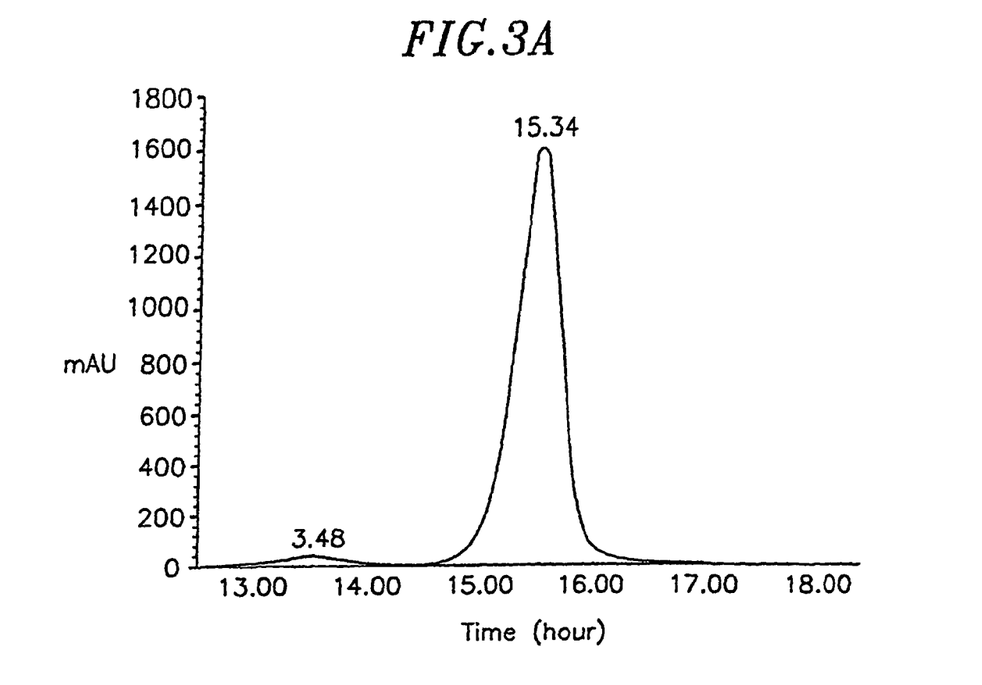
FIGS. 3A and 3B illustrate SEC scans of the Microparticle 2 extract solution obtained in Test Example 2 and a standard hGH aqueous solution, respectively.
Figure 3B:
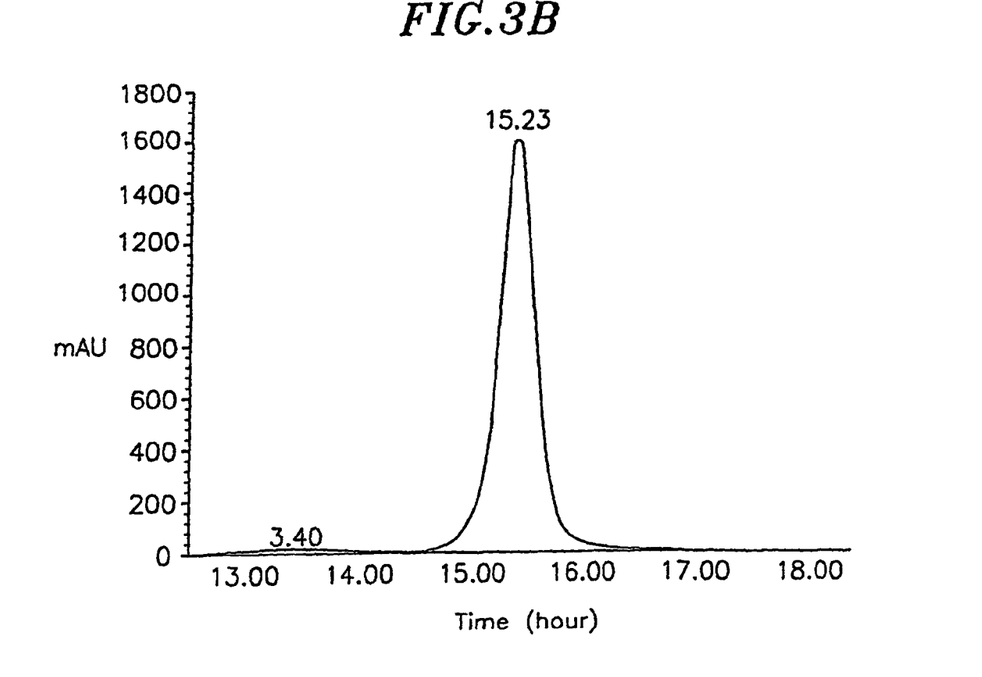

The solid lipophilic microparticle of the present invention comprises a lipophilic substance, hyaluronic acid or an inorganic salt thereof and an active ingredient.

The active ingredient which may be used in the present invention is a protein drug or a peptide drug. Representative protein or peptide drugs include human growth hormone, bovine growth hormone, porcine growth hormone, growth hormone releasing hormone, growth hormone releasing peptide, granulocyte-colony stimulating factor, granulocyte macrophage-colony stimulating factor, macrophage-colony stimulating factor, erythropoietin, bone morphogenic protein, interferon, insulin, atriopeptin-Ill, monoclonal antibody, tumor necrosis factor, macrophage activating factor, interleukin, tumor degenerating factor, insulin-like growth factor, epidermal growth factor, tissue plasminogen activator and urokinase, but these do not limit the protein or peptide drugs which may be used in the present invention.

Hyaluronic acid or an inorganic salt thereof of the present invention is used for coating the active ingredient at first to form a solid microparticle. Representative inorganic salt of hyaluronic acid includes sodium hyaluronate, potassium hyaluronate, ammonium hyaluronate, calcium hyaluronate, magnesium hyaluronate, zinc hyaluronate and cobalt hyaluronate. Hyaluronic acid or its inorganic salt may be used in an amount ranging from 0.1 to 99% by weight based on the weight of the microparticle.

The lipophilic substance, which may be used in the present invention, includes a lipid and its derivatives, a fatty acid and its derivatives, a wax and a mixture thereof. Representative lipids include lecithin, phosphatidylcholine, phosphatidylethanolamine, phosphatidylserine and phosphatidylinositol. Representative derivatives of lipid include arachidoyl phosphatidylcholine and stearoyl phosphatidylcholine. Representative fatty acids include myristic acid, palmitic acid, stearic acid, and salts thereof. Representative derivatives of fatty acid include glyceryl stearate, sorbitan palmitate, sorbitan stearate, sorbitan monooleate and polysorbate. Representative waxes include an anionic emulsifying wax, carnauba wax and microcrystalline wax. Among those, more preferred are surface-active lipophilic substances such as lecithin, phosphatidylcholine and phosphatidylethanolamine, which will be illustrated herein later.

The lipophilic microparticle of the present invention may comprise 0.001 to 99% by weight, preferably 0.1 to 10% by weight, of an active ingredient and 1 to 99.999% by weight, preferably 5 to 50% by weight, of an lipophilic substance, based on the weight of the microparticle.

The solid lipophilic microparticle of the present invention may further comprise a water-soluble excipient as a stabilizer for the purpose of stabilizing the active ingredient. The water-soluble excipient as a stabilizer which may be used in the present invention includes a protein such as albumin and gelatin; an amino acid such as glycine, alanine, glutamic acid, arginine, lysine and a salt thereof; carbohydrate such as glucose, xylose, galactose, fructose, maltose, saccharose, dextran, mannitol, sorbitol, trehalose and chondroitin sulfate; an inorganic salt such as phosphate; a surfactant such as Tween® (ICI), poly(ethylene glycol) and a mixture thereof. The stabilizer may be used in an amount ranging from 0.001 to 99% by weight, preferably from 0.1 to 50% by weight based on the amount of the microparticle.

The solid lipophilic microparticle of the present invention may be prepared by combining a solution of a lipophilic substance with hyaluronic acid or an inorganic salt thereof and an active ingredient selected from the group consisting of a protein drug and a peptide drug and spray-drying the resulting mixture.

In the most preferred embodiment of the invention, the solid lipophilic microparticle of the present invention is prepared by dissolving an active ingredient in an aqueous solution containing hyaluronic acid or an inorganic salt thereof and other optional component such as the water-soluble excipient, adding the surface-active lipophilic substance such as lecithin thereto to allow it to hydrate, and spray-drying the resulting solution. In the spray-drying step, the surface-active lipophilic substance migrates to the surface of the droplets and coats the particles containing the active ingredient.

The reason that the spray-drying process of a mixture of the above three components can provide microparticles having the lipophilic surface may be based upon the below theoretical illustration.

When an aqueous solution, containing an active ingredient, HA (hyaluronic acid or inorganic salt thereof) and lecithin, is subjected to spray-drying, the solution first floats in a form of fine droplets. While these droplets fall slowly within a cyclone filled with hot air, water is vaporized so that the droplets are dried to become solid spheres. Since the droplet is a liquid sphere of micrometer size, it has a high surface tension and thus lecithin as a surfactant, contained therein, can reduce the surface tension of droplet. The surfactant has both a hydrophilic portion and lipophilic portion in one molecule. As such, when the surfactant is in the interface of a hydrophilic phase (e.g., aqueous solution) and lipophilic phase (e.g., lipid layer or air layer), the hydrophilic portion of surfactant molecule orients toward the hydrophilic phase whereas the lipophilic portion thereof orients toward the lipophilic phase, whereby the thermodynamic stability can be achieved. Accordingly, when a droplet is formed by spray drying, lecithin as a surfactant moves toward the surface of the droplet and then orient so that the surface tension is reduced thereby achieving the thermodynamic stability. This state is maintained even while water is vaporized and thus lecithin remains on the surface of microparticle. As a result, the solid lipophilic microparticle of the present invention is endowed with an improved dispersability in a lipophilic medium such as an oil, giving an improved injectability.

Alternatively, the solid lipophilic microparticle of the present invention may be prepared by two-step drying, combining a solution of hyaluronic acid or an inorganic salt thereof and an active ingredient selected from the group consisting of a protein drug and a peptide drug, spray-drying the resulting mixture to form particles, then dispersing the particles in a solution of lipophilic substance, and spray-drying the resultant mixture. More specifically, the solid lipophilic microparticle is prepared by dissolving an active ingredient in an aqueous solution containing hyaluronic acid or an inorganic salt thereof and other optional component such as the water-soluble excipients; spray-drying the resulting solution to obtain solid particles containing the active ingredient; dispersing the solid particles in an organic solvent containing a lipophilic substance; and then drying the dispersion to obtain solid lipophilic microparticles.

The organic solvent which may be used in the above procedure includes ethanol, methylene chloride and isopropyl alcohol. By the above procedure, direct contact of the active ingredient to organic solvent during the manufacturing process can be avoided.

The inventive microparticle thus prepared has an average particle size ranging from 0.1 to 200 μm, preferably from 1 to 50 μm, more preferably 1 to 10 μm.

The solid lipophilic microparticle of the present invention may thereafter be formulated in the forms of dispersion, emulsion and aerosol.

Therefore, the present invention further provides a dispersion formulation prepared by dispersing the inventive solid lipophilic microparticles in a lipophilic medium. The solid lipophilic medium which may be used in the present invention includes an edible oil, mineral oil, squalene, squalane, cod liver oil, mono-, di- or triglyceride, and a mixture thereof. Representative edible oils include corn oil, olive oil, soybean oil, safflower oil, cotton seed oil, peanut oil, sesame oil, sunflower oil and a mixture thereof. The lipophilic medium may further comprise a dispersing agent or a preservative. The dispersion formulation may be used for injection or oral administration.

The present invention also provides an oil-in-water emulsion formulation comprising an aqueous injection medium and the dispersant formulation. The aqueous injection medium includes distilled water and a buffered solution. In the emulsion formulation, the solid lipophilic microparticles are coated with an oil and remain in the oil phase while enhancing the formation and stabilization of the water-in-oil emulsion. The emulsion formulation may be used for injection.

The present invention further provides an aerosol formulation comprising the inventive microparticle. The aerosol formulation may be prepared according to a conventional method using a conventional excipient. The aerosol formulation may be administered via nasal or bronchial mucous membrane. The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

Example 1

Preparation of Solid Lipophilic Microparticles

Human growth hormone (hGH) was dissolved in 5 mM PBS to a concentration of 2 mg/ml and then Tween 80 was added thereto in an amount of 0.01 wt % based on the weight of PBS. Sodium hyaluronate having a molecular weight of 1,000,000 was dissolved therein to a concentration of 0.2% (w/v). The resulting solution was provided to a spray dryer (Buchi 190) at a flow rate of 3 ml/minute to obtain primary particles. In this step, the inflow air temperature was 85° C. The average particle size of the primary particles thus obtained was 3 μm.

Lecithin was dissolved in ethanol to a concentration of 1% (w/v) and then the primary particles were suspended therein at a concentration of 1% (w/v). The resulting suspension was provided to a spray dryer (Buchi 190) to obtain microparticles (Microparticle 1). The average particle size of the microparticles thus obtained was 7 μm.

Examples 2 to 14

Preparation of Solid Lipophilic Microparticles

The procedure of Example 1 was repeated using various ingredients listed in Table I to obtain various solid microparticles (Microparticles 2 to 14).

TABLE I

| Microparticle No. | Primary Particle | | | | | Microparticle | | | Average Particle Size (μm) |
|---|---|---|---|---|---|---|---|---|---|
| | Active Ingredient | Water-soluble Excipient | Sodium Hyaluronate (½ (w/v)/MW) | Inflow Air Temp. (° C.) | Average Particle Size (μm) | Primary Particle (% (w/v)) | Lipophilic Substance | Solvent | |
| 1 | 2 mg/ml hGH | 0.01 wt % Tween 80 | 0.2% (w/v)/ MW: 1,000,000 | 85 | 3 | 1 | 1% (w/v) Lecithin | Ethanol | 7 |
| 2 | 1 mg/ml hGH | 0.01 wt % Tween 80 | 0.1% (w/v)/ MW: 2,000,000 | 85 | 2 | 1 | 1% (w/v) Lecithin | Ethanol | 5 |
| 3 | 1 mg/ml hGH | 0.01 wt % Tween 80 | 0.09% (w/v)/ MW: 2,000,000 | 85 | 2 | 1 | 1% (w/v) Lecithin | Ethanol | 5 |
| 4 | 2 mg/ml bST[a] | 0.01 wt % Tween 80 | 0.2% (w/v)/ MW: 2,000,000 | 85 | 3 | 2 | 1% (w/v) Lecithin | Ethanol | 7 |
| 5 | 2 mg/ml pST[b] | 0.01 wt % Tween 80 | 0.2% (w/v)/ MW: 2,000,000 | 85 | 3 | 1 | 1% (w/v) Lecithin | Ethanol | 7 |
| 6 | 0.4 mg/ml GM-CSF[c] | 0.01 wt % Tween 80 | 0.16% (w/v)/ MW: 2,000,000 | 85 | 3 | 1 | 1% (w/v) Lecithin | Ethanol | 7 |
| 7 | 1,000 IU/ml EPO[d] | 0.01 wt % Tween 80, & 0.5 mg/ml Serum Albumin | 0.25% (w/v)/ MW: 2,000,000 | 85 | 3.5 | 1 | 1% (w/v) Lecithin | Ethanol | 7 |
| 8 | 200,000 IU/ml Interferon-α | 0.01 wt % Tween 80, 0.2 mg/ml D-mannitol, & 0.2 mg/ml Serum Albumin | 0.25% (w/v)/ MW: 2,000,000 | 105 | 3.5 | 1 | 1% (w/v) Lecithin | Ethanol | 7 |
| 9 | 200,000 IU/ml Interferon-γ | 0.01 wt % Tween 80, 0.2 mg/ml Glycine, & 0.2 mg/ml Serum Albumin | 0.25% (w/v)/ MW: 2,000,000 | 105 | 3.5 | 1 | 1% (w/v) Lecithin | Ethanol | 7 |
| 10 | 20 IU/ml Insulin | 0.01 wt % Tween 80 | 0.2% (w/v)/ MW: 2,000,000 | 85 | 3 | 1 | 1% (w/v) Lecithin | Ethanol | 7 |
| 11 | 2 mg/ml IGF-I[e)] | 0.01 wt % Tween 80 | 0.2% (w/v)/ MW: 2,000,000 | 85 | 3 | 1 | 1% (w/v) Lecithin | Ethanol | 7 |
| 12 | 1 mg/ml hGH | 0.01 wt % Tween 80 | 0.1% (w/v)/ MW: 2,000,000 | 85 | 2 | 1 | 0.5% (w/v) Stearic Acid | Methylene Chloride | 6 |
| 13 | 1 mg/ml hGH | 0.01 wt % Tween 80 | 0.1% (w/v)/ MW: 2,000,000 | 85 | 2 | 1 | 0.5% (w/v) Sorbitan Monostearate | Isopropyl Alcohol | 7 |
| 14 | 1 mg/ml hGH | 0.01 wt % Tween 80 | 0.1% (w/v)/ MW: 2,000,000 | 85 | 2 | 1 | 0.5% (w/v) Glyceryl Monostearate | Methylene Chloride | 7 |

[a)] bovine somatotropin
[b)] porcine somatotropin
[c)] granulocyte macrophage-colony stimulating factor
[d)] erythropoietin
[e)] insulin-like growth factor-I

Example 15

Preparation of Cotton Seed Oil Dispersion Formulations of Microparticle 2

Microparticle 2 prepared in Example 2 was added to cotton seed oil using a magnetic stirrer to obtain five cotton seed oil dispersions each containing 200, 360 and 500 mg/ml of Microparticle 2, respectively.

Example 16

Preparation of Edible Oil Dispersion Formulations of Microparticle 2

The procedure of Example 15 was repeated using Microparticle 2 to obtain soybean oil, corn oil and sesame oil dispersions each containing 100 mg/ml of Microparticle 2.

Example 17

Preparation of Edible Oil Dispersion Formulations of Microparticle 4

The procedure of Example 15 was repeated using Microparticle 4 to obtain cotton seed oil, soybean oil, corn oil and sesame oil dispersions each containing 360 mg/ml of Microparticle 4.

Example 18

Preparation of Edible Oil Dispersion Formulations of Microparticle 5

The procedure of Example 15 was repeated using Microparticle 5 to obtain cotton seed oil, soybean oil, corn oil and sesame oil dispersions each containing 360 mg/ml of Microparticle 5.

Example 19

Preparation of Edible Oil Dispersion Formulations of Microparticle 8

The procedure of Example 15 was repeated using Microparticle 8 to obtain cotton seed oil, soybean oil, corn oil and sesame oil dispersions each containing 360 mg/ml of Microparticle 8.

Example 20

Preparation of Emulsion Formulations of Microparticle 2

Each of cotton seed oil dispersions obtained in Example 2 was added to five different volumes of 0.9% NaCl solution to obtain different mixtures of oil and water containing Microparticle 2.

As results, obtained five homogeneous, white-opaque oil-in-water emulsions respectively contained 5, 20, 50, 120 and 200 mg/ml of Microparticle 2, and the oil to the water ratios thereof are 1:9, 1:4, 1:3, 1:2, and 2:3, respectively.

In these emulsion formulations, the solid microparticles were dispersed in the oil phase and the oil droplets containing the microparticles were stable due to the lipophilic surface of the microparticles. The emulsions were stable at an ambient temperature for a period of over 2 weeks.

Example 21

Preparation of Emulsion Formulations of Microparticle 2

The procedure of Example 20 was repeated using the soybean oil, corn oil and sesame oil dispersions obtained in Example 16 to obtain homogeneous, white-opaque oil-in-water emulsion formulations.

Example 22

Preparation of Emulsion Formulation of Microparticle 12

The procedure of Example 15 was repeated using Microparticle 12 and soybean oil to obtain a soybean oil dispersion containing 100 mg/ml of Microparticle 12. Using the resulting dispersion, the procedure of Example 20 was repeated to obtain a homogeneous, white-opaque oil-in-water emulsion formulation.

Example 23

Preparation of Emulsion Formulation of Microparticle 13

The procedure of Example 15 was repeated using Microparticle 13 and soybean oil to obtain a soybean oil dispersion containing 100 mg/ml of Microparticle 13. Using the resulting dispersion, the procedure of Example 20 was repeated to obtain a homogeneous, white-opaque oil-in-water emulsion formulation.

Example 24

Preparation of Emulsion Formulation of Microparticle 14

The procedure of Example 15 was repeated using Microparticle 14 and soybean oil to obtain a soybean oil dispersion containing 100 mg/ml of Microparticle 14. Using the resulting dispersion, the procedure of Example 20 was repeated to obtain a homogeneous, white-opaque oil-in-water emulsion formulation.

Example 25

Preparation of Emulsion Formulations of Microparticle 4

The procedure of Example 20 was repeated using the cotton seed oil, soybean oil, corn seed oil and sesame oil dispersions obtained in Example 17 and 2-fold volumes of 0.9% NaCl solution to obtain four homogeneous, white-opaque oil-in-water emulsion formulations. Each of the formulations thus obtained contained 120 mg/ml of Microparticle 4 in a mixture of oil and water (1:2).

Example 26

Preparation of Emulsion Formulations of Microparticle 5

The procedure of Example 20 was repeated using the cotton seed oil, soybean oil, corn seed oil and sesame oil dispersions obtained in Example 18 and 2-fold volumes of 0.9% NaCl solution to obtain four homogeneous, white-opaque oil-in-water emulsion formulations. Each of the formulations thus obtained contained 120 mg/ml of Microparticle S in a mixture of oil and water (1:2).

Example 27

Preparation of Emulsion Formulations of Microparticle 8

The procedure of Example 20 was repeated using the cotton seed oil, soybean oil, corn seed oil and sesame oil dispersions obtained in Example 19 and 2-fold volumes of 0.9% NaCl solution to obtain homogeneous, white-opaque oil-in-water emulsion formulations of Microparticle 8. Each of the formulations thus obtained contained 120 mg/ml of Microparticle 8 in a mixture of oil and water (1:2).

Comparative Example 1

Preparation of Comparative Microparticle 1

The procedure of Example 2 was repeated using 1 mg/ml hGH, 0.1% (w.v) sodium hyaluronate having a molecular weight of 2,000,000 to obtain comparative microparticles having no lipophilic coating (Comparative Microparticle 1).

Comparative Example 2

Preparation of Dispersion Formulation of Comparative Microparticle 1

The procedure of Example 15 was repeated using Comparative Microparticle 1 and cotton seed oil to obtain a cotton seed oil dispersion containing 100 mg/ml of Comparative Microparticle 1 (Comparative Dispersion 1).

Comparative Example 3

Preparation of Emulsion Formulation of Comparative Microparticle 1

The procedure of Example 20 was repeated using Comparative Dispersion 1. The resulting mixture (Comparative Emulsion 1) did not form a homogeneous emulsion and but exhibited a phase separation, with the microparticles dispersed in both the oil and water phases.

Comparative Example 4

Preparation of Comparative Microparticle 2

The procedure of Example 8 was repeated using $2\times10^5$ IU/ml interferon-α, 0.2 mg/ml D-mannitol, 0.2 mg/ml serum albumin and 0.25% (w/v) sodium hyaluronate having a molecular weight of 2,000,000 at an inflow air temperature of 105° C. to obtain a comparative microparticles having no lipophilic coating (Comparative Microparticle 2) which had an average particle size of 3.5 μm.

Comparative Example 5

Preparation of Oil Dispersion Formulation of Comparative Microparticle 2

The procedure of Example 15 was repeated using Comparative Microparticle 2 and cotton seed oil to obtain a cotton seed oil dispersion containing 100 mg/ml of Comparative Microparticle 2 (Comparative Dispersion 2).

Comparative Example 6

Preparation of Emulsion Formulation of Comparative Microparticle 2

The procedure of Example 20 was repeated using Comparative Dispersion 2. The resulting mixture (Comparative Emulsion 2) did not form a homogeneous emulsion but exhibited a phase separation, with the microparticles dispersed in both the oil and water phases.

Test Example 1

In Vitro Release Test of Microparticles 1, 2 and 3

Each of Microparticles 1, 2 and 3 was dispersed in a buffered solution (150 mM NaCl, 10 mM phosphate, 0.05% sodium azide, pH 7.4) so that the hGH concentration was 1.0 mg/ml. An in vitro release test was conducted by stirring the resulting dispersion at 37° C. and at a preset time, the dispersion was centrifuged at 800 g for 10 minute and a sample of the supernatant taken in an amount of 1/10 volume of the dispersion was mixed with an equal volume of the above buffered solution. hGH contained in the supernatant was quantified using Lowry method with High Performance Liquid Chromatography (HPLC).

FIG. 1 shows the release profiles of Microparticles 1, 2 and 3 thus determined. As can be seen from FIG. 1, as the molecular weight of hyaluronic acid becomes higher, and as the content of hGH decrease, the release rate of hGH becomes slower. Therefore, the protein drug release rate can be controlled by adjusting the molecular weight of hyaluronic acid and the protein drug content. Further, in vitro release test results showed that an initial burst release of the protein drug does not occur and the release rate is constant until 70% of protein is released.

Test Example 2

Stability test of Microparticle 2

To examine whether hGH contained in Microparticle 2 maintains its activity, the procedure of Test Example 1 was repeated and the amount of hGH released from Microparticle 2 in 48 hours was determined with both reversed phase (RP) HPLC and size exclusion chromatography (SEC). The RP HPLC was used to assess the extent of oxidative and deamidative denaturation of the protein; and SEC, the denaturation of the protein by aggregation.

FIGS. 2A and 2B represent RP HPLC results for the Microparticle 2 extract solution and the hGH aqueous solution used in preparation of Microparticle 2, respectively.

FIGS. 3A and 3B provide SEC results for the Microparticle 2 extract solution and hGH aqueous solution used in the preparation of Microparticle 2, respectively.

As can be seen from FIGS. 2 and 3, the amount of hGH released from the inventive microparticle is identical with that of the original hOH aqueous solution according to the RP HPLC results; and the SEC results show the monomeric hGH content is 95% or more. These results suggest that hGH is not denatured during the preparation of the inventive microparticles.

Test Example 3

In Vitro Release Test of Microparticles 4 to 11

The procedure of Test Example 1 was repeated using each of Microparticles 4 to 11, and the cumulative amounts of the drug released in 10 and 72 hours as well as the monomeric protein content of the 72 hours sample were determined. The results are shown in Table II.

TABLE II

| Microparticle No. | Released Amount (%) at 10 hours | Released Amount (%) at 72 hours | Monomer Content (%) |
|---|---|---|---|
| 4 | 45 | 92 | 94 |
| 5 | 47 | 87 | 89 |
| 6 | 44 | 89 | 97 |
| 7 | 32 | 76 | 95 |
| 8 | 54 | 92 | 94 |
| 9 | 49 | 88 | 95 |
| 10 | 60 | 95 | 95 |
| 11 | 38 | 93 | 97 |

As can be seen from Table II, the microparticles of the present invention release the protein drug over a period of 3 days, with no sign of denaturation of the protein drug.

Test Example 4

Injectability Test 1

To examine whether the microparticles of the present invention are homogeneously dispersed in an oil dispersion or in an oil-water emulsion, injectability tests were conducted. The injectability is defined as the force required to push a syringe filled with a test sample at a velocity of 80 mm/minute.

The procedure was carried out 0.9% NaCl aqueous solution, cotton seed oil, the cotton seed oil dispersion of Example 15, the emulsion of Example 20, Comparative Dispersion 2, and Comparative Emulsion 2, using a 26 gauge syringe needle. Results are shown in Table III.

TABLE III

| Formulation | Conc. Of Microparticle (mg/ml) | Injectability (kg$_f$) |
|---|---|---|
| 0.9% NaCl Aqueous Solution | 0 | 0.1 |
| Cotton seed oil | 0 | 1.6 |
| Dispersion of Example 15 | 100 | 1.7 |
| Emulsion of Example 20 | 120 | 0.8 |
| Comparative Dispersion 1 | 100 | 10.5 |
| Comparative Emulsion 1 | 20 | 23.3 |

As can be seen from Table III, Microparticle 2 of the present invention has good dispersibility in cotton seed oil due to the lipophilic lecithin coating, and the cotton seed oil dispersion of the present invention has an injectability equivalent to that of the cotton seed oil. Further, the emulsion of Example 20 has a lower injectability than cotton seed oil in spite of the high concentration of Microparticle 2.

In contrast, Comparative Microparticle 1 has an inferior dispersibility in cotton seed oil due to the absence of a lipophilic coating, causing the poor injectability of Comparative Dispersion 1. Further, when the hydrophilic surface of Comparative Microparticle 1 caused a phase separation in Comparative Emulsion 1, with a consequential leaching of the sodium hyaluronate component into the aqueous phase to raise the viscosity of water layer. Therefore, Comparative Emulsion 1 has an even poorer injectability than Comparative Dispersion 1.

Test Example 5

Injectability Test 2

The procedure of the Test Example 4 was repeated for the emulsions obtained in Examples 22 to 24, and soybean oil as a control. The injectability of soybean oil was 1.4 kg$_f$, and those of the emulsions obtained in Examples 22 to 24 were in the range of 0.3 to 0.5 kg$_f$, similar to that of 0.9% NaCl aqueous solution. The lipophilic surface of the microparticles of the present invention becomes coated with soybean oil, resulting in a homogeneous oil-in-water emulsion which has an injectability equivalent to that of water.

Test Example 6

Animal Test

The effect administering of the inventive formulation containing hGH was examined using 7 weeks-old female dwarf rats (body weight: approximate 100 g) which have the heredity of low growth hormone secretion.

The dispersion of Examples 15, the emulsion of Example 20, Comparative Dispersion 1, Comparative Emulsion 1, and Eutroprin® (LG Chemical Ltd., Korea), an aqueous formulation were chosen for the test, and each was administered to a group of 10 dwarf rats at an hGH dose of 350 μg per rat and then the weight gain was examined. As a control, rats which did not receive hGH were used. The average cumulative net weight gains are shown in Table IV.

TABLE IV

| | Day | | | | | | (unit: g) |
|---|---|---|---|---|---|---|---|
| | 1 | 2 | 3 | 4 | 5 | 6 | |
| Control | 0.9 | 2.7 | 3.6 | 4.7 | 6.3 | 7.5 | |
| Eutroprin ® | 4.7 | 4.2 | 5.3 | 6.4 | 7.1 | 8.5 | |
| Comparative Dispersion 1 | 5.0 | 5.7 | 7.2 | 8.5 | 10.2 | 11.5 | |
| Comparative Emulsion 1 | 4.3 | 4.9 | 3.6 | 5.4 | 6.7 | 7.8 | |
| Dispersion of Example 15 | 5.5 | 6.6 | 7.3 | 8.7 | 11.4 | 12.3 | |
| Emulsion of Example 20 | 5.3 | 6.8 | 8.1 | 9.2 | 11.3 | 13.0 | |

As can be seen from Table IV, the average weight of the rats in the Eutropin® increased on the 1st day, but it decreased on the 2nd day. The weight increased thereafter at a rate similar to that of the control group.

The average weight of the rats in the Comparative Dispersion 1 group continuously increased while that of the rats in the Comparative Emulsion 1 group decreased on the 3rd day. Because the microparticles in Comparative Emulsion 1 have a hydrophilic surface, the drug dissolves, and therefore, it has a weight gain effect equal to that of the aqueous formulation, Eutropin®.

In contrast, the average weight of the rats administered with the dispersion of Example 15 and the emulsion of Example 20 increased for 6 days at higher rates than either Comparative Dispersion 1 or Comparative Emulsion 1. The microparticles of the present invention having lecithin coatings are covered with cotton seed oil even after injection, and absorb water only slowly, thereby releasing the drug at a constant rate.

Test Example 7

Animal Test

The dispersion of Example 17 and the emulsion of Examples 25 were each administered to 7 weeks-old female dwarf rats (body weight: approximate 100 g) at a bST dosage of 12.5 mg per rat and then their weight gains were examined. As a control, rats which did not receive bST were used. The net average cumulative weight gains are shown in Table V.

TABLE V

|  | DAY | | | | | | | (unit: g) |
| --- | --- | --- | --- | --- | --- | --- | --- | --- |
|  | 1 | 2 | 3 | 4 | 5 | 6 | 8 | 10 |
| Control | 1.4 | 2.9 | 4.6 | 6.1 | 6.5 | 7.2 | 8.8 | 10.4 |
| Dispersion of Example 17 | 10.3 | 10.8 | 14.9 | 18.1 | 19.4 | 20.6 | 22.2 | 22.7 |
| Emulsion of Example 25 | 9.7 | 11.5 | 14.6 | 17.7 | 19.9 | 20.8 | 22.5 | 22.9 |

As can be seen from Table V, the average weight of rats administered with either the dispersion of Example 17 or the emulsion of Example 25 increased continuously for 6 days and the rate of daily weight gain was higher than the control group. After 8 days, the weight gain became insignificant, suggesting that the drug release time is about 8 days in both case.

Test Example 8

Cytopathic Effect Inhibition Test

The emulsion of Example 27, Comparative Dispersion 2, interferon-$\alpha$ aqueous formulation were each administered to 5 months-old rabbits (body weight: 2.5 kg) at an interferon-$\alpha$ dosage of 300 µg.
The blood level of the drug was determined using a cytopathic effect inhibition test, which was conducted by treating cells with interferon-$\alpha$, adding virus thereto and then determining inhibition of the cell pathology. Male calf kidney cell (MDBO CATCC CCF-22) and vesicular stomatitis virus (ATCC VR 158) were used in the test. Titers of interferon-$\alpha$ in the blood were measured for 5 days and the results are shown in Table VI.

TABLE VI

|  | 7 hours | Day 1 | DAY 2 | Day 3 | Day 4 | Day 5 |
| --- | --- | --- | --- | --- | --- | --- |
| Aqueous Formulation | $1.4 \times 10^3$ | $1.2 \times 10$ | ND* | ND | ND | ND |
| Comparative Dispersion 2 | $2.1 \times 10^3$ | $2.6 \times 10^3$ | $9.1 \times 10^2$ | $3.4 \times 10^2$ | $1.7 \times 10^2$ | $1.5 \times 10$ |
| Emulsion of Example 27 | $1.7 \times 10^3$ | $2.2 \times 10^3$ | $1.1 \times 10^3$ | $4.6 \times 10^2$ | $2.8 \times 10^2$ | $8.7 \times 10$ |

*not detected

As can be seen from Table VI, the titers of interferon-$\alpha$ for the rats administered with the emulsion of Example 27 were high for the entire test period of 5 days, showing higher levels of interferon-$\alpha$ as compared with the Comparative Dispersion 2 group from day 2. Therefore, the dispersion of the present invention has prolonged release characteristics due to the lipophilic surface of the microparticles.

Comparative Test Example 1 hGH was dissolved in 5 mM PBS to a concentration of 2.3 mg/ml and then sodium hyaluronate having a molecular weight of 2,000,000 was dissolved therein to a concentration of 2% (w/v) to obtain a hyaluronic acid gel formulation.
An in vitro release test was conducted using the gel formulation by repeating the procedure of Test Example 2. As a result, 100% of hGH was released into the supernatant within 1 hour. Therefore, this gel formulation has a drug release time which is much shorter than the microparticles of the present invention.

Comparative Test Example 2

Animal Test

The procedure for preparing a hyaluronic acid gel formulation in Comparative Test Example 1 was repeated using 1.5 mg/ml hGH to obtain a hyaluronic acid gel formulation having no fluidity.
The gel formulation thus obtained was administered to dwarf rats at a hGH dosage of 150 µg per rat and then the average weight gain was examined for 6 days. As a comparative formulation, an aqueous solution formulation, Eutropin® was administered to rats at the same hGH dosage. As a control, rats which did not receive hGH were used. Results expressed in cumulative weight gains are shown in Table VII.

TABLE VII

|  | Day | | | | | |
| --- | --- | --- | --- | --- | --- | --- |
| Group | 1 | 2 | 3 | 4 | 5 | 6 |
| Control | 1.6 | 2.4 | 4.1 | 4.8 | 6.2 | 8.1 |
| Gel Formulation | 3.2 | 3.6 | 3.0 | 6.1 | 6.7 | 7.7 |
| Eutropin ® | 3.3 | 2.6 | 4.2 | 6.4 | 7.8 | 8.3 |

As can be seen from Table VII, the average weight gain of the rats administered with the gel formulation is similar to that of the Eutropin® group. The rate of weight gain after 2 days was not significantly different among the three groups, suggesting that the drug release from the gel formulation does not lasted more than 1 day.

Comparative Test Example 3 hGH was dissolved in 5 mM PBS to a concentration of 2 mg/ml and then Tween 80 was added thereto to a concentration of 0.01 wt %. The resulting solution was provided to a spray dryer (Buchi 190) at a flow rate of 3 ml/minute to obtain microparticles. In this step, the inflow air temperature was 85° C. The average particle size of the microparticles thus prepared was 2.5 μm.

Benzyl hyaluronate was dissolved in dimethyl sulfoxide (DMSO) to a concentration of 6% and then the microparticles were dispersed therein. The resulting dispersion was added to a mineral oil containing Aracel ATM (Atlas Chemical Ind.). The mixture was homogenized to obtain a microemulsion. The microemulsion was composed of the mineral oil as a continuous phase and the benzyl hyaluronate/DMSO solution as a dispersed phase.

Ethyl acetate was added to the microemulsion while stirring to extract DMSO from the dispersed phase, giving benzyl hyaluronate microparticles containing hGH. The average particle size of the microparticles was 5.5 μm and the content of hGH was 45 wt %.

An in vitro release test was conducted using the benzyl hyaluronate formulation thus obtained by repeating the procedure of Test Example 2 and the cumulative amounts of hGH released are shown in Table VIII.

TABLE VIII

| | Hours | | | | | | | |
|---|---|---|---|---|---|---|---|---|
| | 0 | 1 | 3 | 5 | 7 | 24 | 48 | 72 | 144 |
| Releasing Amount (%) | 0 | 15 | 21 | 23 | 25 | 27 | 28 | 30 | 30 |

As can be seen from Table VIII, the benzyl hyaluronate formulation released hGH only slightly after 5 hours and only 30% of the loaded hGH was released in 144 hours. Thus, most of hGH in the benzyl hyaluronate formulation is bound in the benzyl hyaluronate matrix and not released.

The above benzyl hyaluronate formulation was dispersed in cotton seed oil and the resulting dispersion was administered to dwarf rats at a hGH dosage of 300 μg per rat. The average weight gain was determined and the results expressed in cumulative weight gain are shown in Table VIII.

TABLE IX

| | Day | | | | | | |
|---|---|---|---|---|---|---|---|
| Formulation | 1 | 2 | 3 | 4 | 5 | 6 | 7 |
| Control | 1.2 | 2.3 | 3.6 | 5.7 | 6.6 | 7.3 | 8.2 |
| Hyaluronic Acid-Benzyl Ester Formulation | 3.6 | 2.7 | 5.4 | 6.3 | 7.1 | 8.4 | 8.0 |

As can be seen from Table IX, formulation shows no significant effect of the benzyl hyaluronate after day 1.

Example 28

Preparation of Spray-Dried Microparticles Containing hGH

Lecithin was hydrated in deionized water to a concentration of 5 mg/ml, and then the resulting mixture was passed through a microfluidizer to prepare a lecithin suspension in which lecithin particles having a particle size of 50~100 nm were homogeneously suspended. Human growth hormone (hGH) was dissolved in 5 mM PBS to a concentration of 30~50 mg/ml. Sodium hyaluronate having a molecular weight of 3,000,000 was dissolved in deionized water to a concentration of 4.5 mg/ml, and then the lecithin suspension and hGH solution as prepared above were added thereto so that a final concentration of sodium hyaluronate was 3 mg/ml, a final concentration of lecithin was 0.5 mg/ml, and a final concentration of hGH was 1 mg/ml, respectively.

The resulting solution was provided to a spray dryer (Buchi 190) at a flow rate of 1 ml/minute to obtain microparticles. In this procedure, the temperature of inflow dry air was 85° C. and the particle size of the microparticles thus obtained was 2~10 μm.

Comparative Example 7

Preparation of Freeze-Dried Particles Containing hGH

Lecithin was hydrated in deionized water to a concentration of 5 mg/ml, and then the resulting mixture was passed through a microfluidizer to prepare a lecithin suspension in which lecithin particles having a particle size of 50~100 nm were homogeneously suspended. HGH was dissolved in 5 mM PBS to a concentration of 30~50 mg/ml. Sodium hyaluronate having a molecular weight of 3,000,000 was dissolved in deionized water at a concentration of 4.5 mg/ml, and then the lecithin suspension and hGH solution were added thereto so that a final concentration of sodium hyaluronate was 3 mg/ml, a final concentration of lecithin was 0.5 mg/ml, and a final concentration of hGH was 1 mg/ml, respectively.

The resulting solution was provided to a freeze-dryer (Dura-Dry™) to be subjected to freeze-drying for 48 hours and then pulverized using a ball mill to make freeze-dried particles. The particle size of the freeze-dried particles thus obtained was 10~100 μm.

Example 29

Preparation of Soybean Oil Dispersion Formulation of Spray-Dried Microparticles Containing hGH The microparticles prepared in Example 28 were dispersed in soybean oil to obtain a dispersion containing microparticles of 50 mg/ml.

Comparative Example 8

Preparation of Soybean Oil Dispersion Formulation of Freeze-Dried Particles Containing hGH The freeze-dried particles prepared in Comparative Example 7 were dispersed in soybean oil to obtain a dispersion containing microparticles of 50 mg/ml. The dispersion showed almost non-fluidic property, i.e., very high viscosity.

Test Example 9

Injectability Test

In the present test, the force required to push a syringe filled with a test sample at a velocity of 80 mm/minute was measured to see the injectability. 26 gauge syringe needle was used. The procedure was carried out about soybean oil, the dispersion of Example 29, and Comparative Example 8, and the experimental results are shown in Table X below.

TABLE X

| Formulation | Concentration of Microparticle (mg/ml) | Injectability (kg$_f$) |
|---|---|---|
| Soybean oil | 0 | 0.5 |
| Example 29 | 50 | 0.45 |
| Comparative Example 8 | 50 | Not injectable |

Comparative Example 9

Preparation of Spray-Dried Microparticles Containing Hgh

The procedure of Example 28 was repeated except that sodium hyaluronate was not used to obtain spray-dried microparticles containing hGH and lecithin.

Test Example 10

Stability Test of Microparticles

The microparticles obtained in Comparative Example 9 were dispersed in a buffer solution (150 mM NaCl, 10 mM phosphate, 0.05% sodium azide, pH 7.4) so that the hGH concentration was 1.0 mg/ml. An in vitro release test was conducted by stirring the resulting dispersion at 37° C. and at a preset time, the dispersion was centrifuged at 800 g for 10 minutes and a sample of the supernatant, taken in an amount of ⅒ volume of the dispersion, was mixed with an equal volume of the above buffered solution. The amount of hGH released from the microparticles in 48 hours was determined with both reversed phase (RP) HPLC and size exclusion chromatography (SEC). The RP HPLC was used to assess the extent of oxidative and deamidative denaturation of hGH; and SEC, the denaturation of hGH by aggregation. The experimental result is shown below.

SEC-HPLC Analysis

| | |
|---|---|
| hGH monomer (active) | 26.16% |
| insoluble form (inactive) | 72.97% |
| other impurities | 0.87% |

As seen from the above result, it was ascertained that when microparticles are prepared using only hGH and lecithin, the large amount of hGH contained in the microparticles is denaturized although the microparticles are prepared by spray drying.

While the invention has been described with respect to the above specific embodiments, it should be recognized that various modifications and changes may be made to the invention by those skilled in the art which also fall within the scope of the invention as defined by the appended claims.

The invention claimed is:

1. A solid lipophilic microparticle prepared by spray drying a mixture comprising (i) a lipophilic substance, (ii) hyaluronic acid being dissolved in water or aqueous buffer solution or an inorganic salt thereof being dissolved in water or aqueous buffer solution and (iii) an active ingredient selected from the group consisting of a protein drug and a peptide drug, wherein the microparticle has an average particle size of 0.1 to 200 μm.

2. The solid lipophilic microparticle of claim 1, wherein the drug is selected from the group consisting of human growth hormone, bovine growth hormone, porcine growth hormone, growth hormone releasing hormone, growth hormone releasing peptide, granulocyte-colony stimulating factor, granulocyte macrophage-colony stimulating factor, macrophage-colony stimulating factor, erythropoietin, bone morphogenic protein, interferon, insulin, atriopeptin-Ill, monoclonal antibody, tumor necrosis factor, macrophage activating factor, interleukin, tumor degenerating factor, insulin-like growth factor, epidermal growth factor, tissue plasminogen activator and urokinase.

3. The solid lipophilic microparticle of claim 1, wherein the inorganic salt of hyaluronic acid is selected from the group consisting of sodium hyaluronate, potassium hyaluronate, ammonium hyaluronate, calcium hyaluronate, magnesium hyaluronate, zinc hyaluronate and cobalt hyaluronate.

4. The solid lipophilic microparticle of claim 1, wherein the lipophilic substance is selected from the group consisting of a lipid, a lipid derivative, a fatty acid, a fatty acid derivative, a wax and a mixture thereof.

5. The solid lipophilic microparticle of claim 4, wherein the lipophilic substance is selected from the group consisting of lecithin, phosphatidylcholine and phosphatidylethanolamine.

6. The solid lipophilic microparticle of claim 1, which further comprises a water-soluble excipient as a stabilizer.

7. The solid lipophilic microparticle of claim 6, wherein the water-soluble excipient is selected from the group consisting of glucose, xylose, galactose, fructose, maltose, saccharose, dextran, chondroitin sulfate, mannitol, sorbitol, trehalose, albumin, gelatin, glycine, alanine, glutamic acid, arginine, lysine, surfactant, polyethylene glycol and a mixture of thereof.

8. A dispersion formulation prepared by dispersing the solid lipophilic microparticle of claim 1 in a lipophilic medium.

9. The dispersion formulation of claim 8, wherein the lipophilic medium is an edible oil, mineral oil, squalene, squalane cod liver oil, mono-, di- or triglyceride, or a mixture thereof.

10. The dispersion formulation of claim 9, wherein the edible oil is corn oil, olive oil, soybean oil, safflower oil, cotton seed oil, peanut oil, sesame oil, sunflower oil or a mixture thereof.

11. The dispersion formulation of claim 9, wherein the lipophilic medium further comprises a dispersing agent or a preservative.

12. The dispersion formulation of claim 9, which is used for injection or oral administration.

13. An oil-in-water emulsion formulation comprising an aqueous injection medium and the dispersant formulation of claim 8.

14. The oil-in-water emulsion formulation of claim 13, wherein the aqueous injection medium is distilled water or a buffered solution.

15. An aerosol formulation comprising the solid lipophilic microparticle of claim 1.

16. The solid lipophilic microparticle of claim 1, wherein the solid lipophilic microparticle is prepared by
    dissolving the active ingredient in an aqueous buffer solution containing hyaluronic acid or an inorganic salt thereof and other optional component comprising a water-soluble excipient,
    adding a surface-active lipophilic substance comprising lecithin thereto to allow it to hydrate, and
    spray-drying the resulting solution.

17. The solid lipophilic microparticle of claim 1 prepared by combining a solution of hyaluronic acid or an inorganic salt thereof and the active ingredient, spray-drying the resulting mixture to form particles, dispersing the particles in a solution of a lipophilic substance, and spray-drying the resultant mixture.

* * * * *